United States Patent [19]
Kwon

[11] Patent Number: 5,729,205
[45] Date of Patent: Mar. 17, 1998

[54] AUTOMATIC TRANSMISSION SYSTEM OF AN EMERGENCY SIGNAL AND A METHOD THEREOF USING A DRIVER'S BRAIN WAVE

[75] Inventor: Young-Wook Kwon, Kyeongsangnam-do, Rep. of Korea

[73] Assignee: Hyundai Motor Company, Seoul, Rep. of Korea

[21] Appl. No.: 813,656

[22] Filed: Mar. 7, 1997

[51] Int. Cl.$^6$ ................................................ G08B 23/00
[52] U.S. Cl. .................. 340/573; 128/731; 340/471; 379/39
[58] Field of Search ........................ 340/573, 471; 370/313; 379/38, 39, 50; 128/691, 731, 904; 607/76

[56] References Cited

U.S. PATENT DOCUMENTS

| | | | |
|---|---|---|---|
| 5,213,338 | 5/1993 | Brotz | 128/731 |
| 5,305,370 | 4/1994 | Kearns et al. | 379/39 |
| 5,477,208 | 12/1995 | Henderson et al. | 340/471 |
| 5,649,061 | 7/1997 | Smyth | 128/731 |
| 5,652,570 | 7/1997 | Lepkofker | 340/573 |

*Primary Examiner*—Jeffery Hofsass
*Assistant Examiner*—John Tweel, Jr.
*Attorney, Agent, or Firm*—Christie, Parker & Hale, LLP

[57] ABSTRACT

An automatic transmission system of an emergency signal and a method thereof using a driver's brain wave which enables the police and hospitals, having a network with an earth station, to provide a proper and immediate rescue operation for those involved in an accident by transmitting an emergency signal derived from the driver's brain wave to the earth station via a global positioning system (GPS) satellite if a driver is in critical condition after the accident. The automatic transmission system of an emergency signal using a driver's brain wave includes a brain wave sensing block, an amplifier, an analog/digital converter, a memory, a microcontroller, and a transmission block.

4 Claims, 3 Drawing Sheets

AUTOMATIC TRANSMISSION SYSTEM OF AN EMERGENCY SIGNAL AND A METHOD THEREOF USING A DRIVER'S BRAIN WAVE

BACKGROUND OF THE INVENTION

1. Field of the Invention

The present invention relates to an automatic transmission system of an emergency signal and a method thereof using a driver's brain wave. More particularly, the present invention relates to an automatic transmission system of an emergency signal and a method thereof using a driver's brain wave which enables the police and hospitals, having a network with an earth station, to provide a proper and immediate rescue operation for those involved in an accident by transmitting an emergency signal derived from the driver's brain wave to the earth station via a global positioning system (GPS) satellite if the driver is in critical condition after the accident.

2. Description of the Prior Art

Recently, in the automotive industry, a system has been developed which can provide information to a driver of the best route to a destination by displaying the current location of the driver on a map displayed by a liquid crystal panel mounted to the dashboard or sitting on the driver's seat. The development of a motor navigation system allows an inexperienced driver or a driver who drives on unfamiliar roads to more easily operate the motor vehicle.

Use of the above-mentioned motor vehicle navigation system is spreading rapidly in Japan, and considerable attention is being given to this system as a leading high technology item of the 21th century in the automotive industry. The widespread use of the system is in the initial stage, but it is predicted that the system will be mounted in up to 20% of the motor vehicles manufactured within the next ten years.

Companies which sell motor vehicles having the navigation system include Nissan Motor Company, Toyota Motor Company, Matsuda Motor Company and Mitsubishi Motor Company. Motor vehicles having the navigation system were initially limited to luxury cars, but recently, Pioneer Motor Company has been selling systems in the general automotive market, thereby widening the choice range for consumers.

The biggest advantage of the motor vehicle navigation system lies in that the driver may enjoy driving even when the driver drives on an unfamiliar road. Maps covering all parts of Japan are included in each of the aforementioned systems, and display of all map portions can be enlarged or reduced from the minimum rate of 1:100,000 scale to the maximum rate of 1:10,000 scale by pressing only one button. In addition, since car service centers, resting places and various kinds of public services, as well as highways, are indicated in detail, the driver may find his or her way easily even when he or she goes astray at night.

The above-mentioned motor vehicle navigation system may use a sensor method or a Global Positioning System (GPS) method using an artificial satellite.

The Nissan Motor Company and the Mitsubishi Motor Company systems use the sensor method by which the current location of the motor vehicle is perceived by sensing the driving direction and the driving distance of the motor vehicle by a sensor. However, the sensor method has a disadvantage in that errors occur at an interval of 100 meters when driving long distances.

Accordingly, the Matsuda Motor Company uses the GPS method using a broadcast signal of artificial satellites launched by the U.S. Government, which is then applied to the sensor method to compensate for the errors occurring in the sensor method. Errors arising under the GPS method occur at an interval of 30 to 50 meters.

GPS is the global positioning system using artificial satellites. GPS has been under development by the U.S. Government for military use for about 20 years and now is being applied for commercial purposes. The data necessary for position measurement is modulated by a frequency diffusion method and a modulated signal of 1575.42 MHz is transmitted from the satellite orbiting the earth. A receiver, that is, an earth station, receives the signal from a plurality of satellites (three satellites in the case of two-dimensional position measurement, and four satellites in the case of three-dimensional position measurement), and calculates the time taken for the signal to reach the earth station by a computer, thereby making it possible to obtain the current location of the earth station.

Presently, sixteen satellites orbit the earth, and the two-dimensional position measurement is possible for 22 hours a day. However, 24 satellites will be launched, including spare satellites, and three-dimensional position measurement for use 24 hours a day will be available when the installation of GPS is finished.

As described above, the motor vehicle navigation system using the GPS satellite enables the driver to reach a destination safely by receiving the signal from the satellite using a GPS receiver mounted in the motor vehicle, perceiving the current location of the driver, and indicating the current location of the driver on the map. The accuracy of the GPS receiver depends on a program of a microcomputer, where the architecture of each program is kept confidential by each respective motor company.

As the motor vehicle navigation system using the GPS is gradually being applied for commercial purposes, the automotive industry is focusing on the development of applied products relevant to the GPS to meet the needs of consumers.

For example, a problem exists when there is no one around who can immediately notify hospitals or the police of a driver who is in critical condition after an accident. The problem is more serious when the location of the accident is in a location that is not frequented by other people.

SUMMARY OF THE INVENTION

Accordingly, the object of the present invention is to provide an automatic transmission system of an emergency signal and a method thereof using a driver's brain wave which enables the police and hospitals, having a network with an earth station, to provide a proper and immediate rescue operation for those involved in an accident by transmitting an emergency signal derived from the driver's brain wave to the earth station via a global positioning system (GPS) satellite if the driver is in critical condition after the accident to substantially obviate one or more of the problems due to limitations and disadvantages of the prior art.

To achieve the object and in accordance with the purpose of the invention, an automatic transmission system of an emergency signal using a human driver's brain wave includes a brain wave sensing block for sensing a brain wave generated from the driver and converting the brain wave into an electric brain wave signal; an amplifier for amplifying the electric brain wave signal inputted from the brain wave sensing block; an analog/digital converter for converting the analog brain wave signal inputted from the amplifier into a digital brain wave signal; a memory in which a unique type of brain wave, generated when the life of a driver is in danger, is digitized and stored as the reference brain wave emergency signal; a micro-controller for comparing the brain wave signal inputted from the analog/digital converter with the reference brain wave emergency signal stored in the memory, and producing an information signal about the current location of an accident together with an information signal about an emergency when the life of the driver is in danger; and a transmission block for transmitting the information signal about the emergency and the information signal about the current location of the accident by loading the information signals on a carrier signal of a high frequency.

According to another aspect of the present invention, a method for controlling the automatic transmission of an emergency signal using a driver's brain wave comprises the steps of initializing all system variables when electrical power is applied; determining whether a selection switch is turned ON; reading a brain wave sensing signal when the selection switch is turned ON; determining whether the life of a driver is in danger after comparing the brain wave sensing signal with a reference brain wave emergency signal stored in a memory; and transmitting a wireless signal about an emergency when the life of the driver is in danger.

Additional objects and advantages of the invention are set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, illustrate one embodiment of the invention and, together with the description, serve to explain the principles of the invention.

In the drawings.

DESCRIPTION OF THE PREFERRED EMBODIMENT

Reference will now be made in detail to the preferred embodiment of the present invention, an example of which is illustrated in the accompanying drawings.

Figure 1:
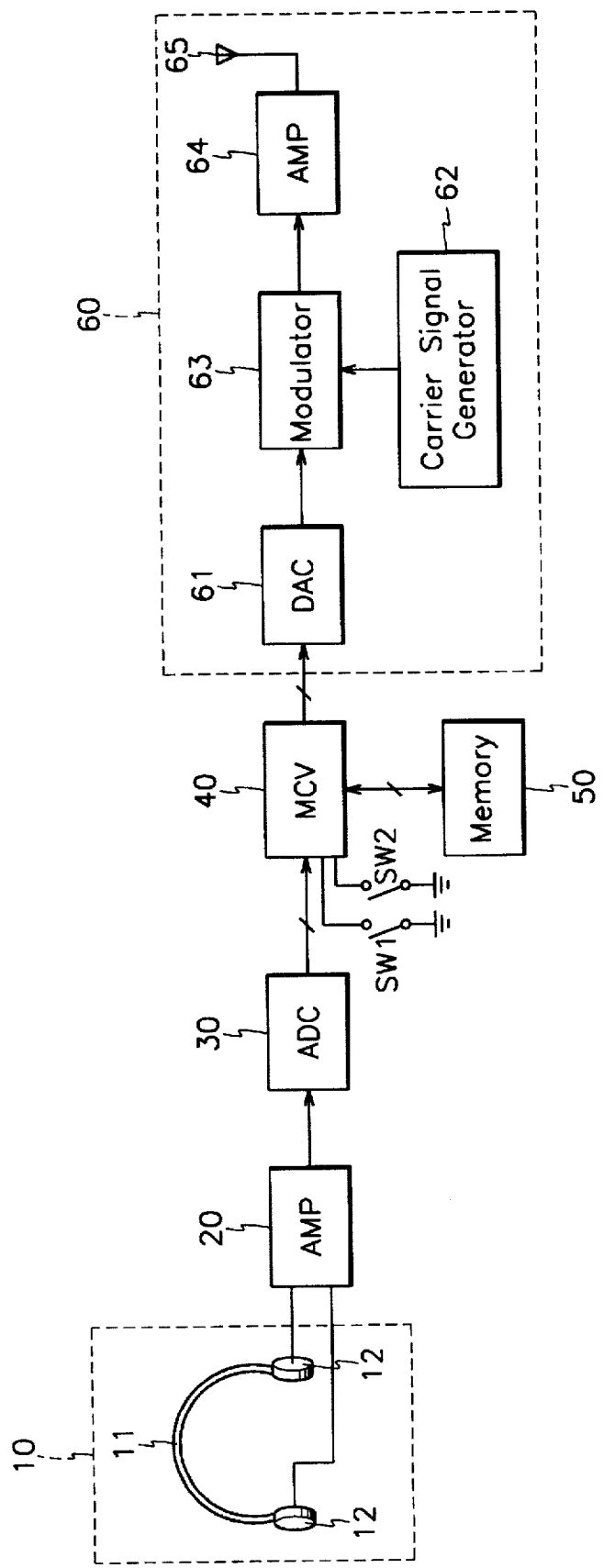
FIG. 1 is a block diagram illustrating an automatic transmission system using a driver's brain wave in accordance with the preferred embodiment of the present invention.

FIG. 1 is a block diagram illustrating an automatic transmission system using a driver's brain wave in accordance with the preferred embodiment of the present invention.

Referring to FIG. 1, the automatic transmission system of an emergency signal using a driver's brain wave includes a brain wave sensing block 10; an amplifier 20 with an input terminal connected to an output terminal of the brain wave sensing block 10; an analog/digital converter (ADC) 30 with an input terminal connected to an output terminal of the amplifier 20; a selection switch SW1 and a forced transmission switch SW2; a micro-controller (MCV) 40 with an input terminal connected to output terminals of the analog/digital converter 30, the selection switch SW1 and the forced transmission switch SW2; a memory 50 connected to the micro-controller 40; and a transmission block 60 with an input terminal connected to an output terminal of the micro-controller 40.

The transmission block 60 includes a digital/analog converter (DAC) 61 with an input terminal connected to the output terminals of the micro-controller 40; a carrier signal generator 62; a modulator 63 with an input terminal connected to output terminals of the digital/analog converter 61 and the carrier signal generator 62; an amplifier 64 with an input terminal connected to an output terminal of the modulator 63; and an antenna 65 connected to an output terminal of the amplifier 64.

Figure 2:
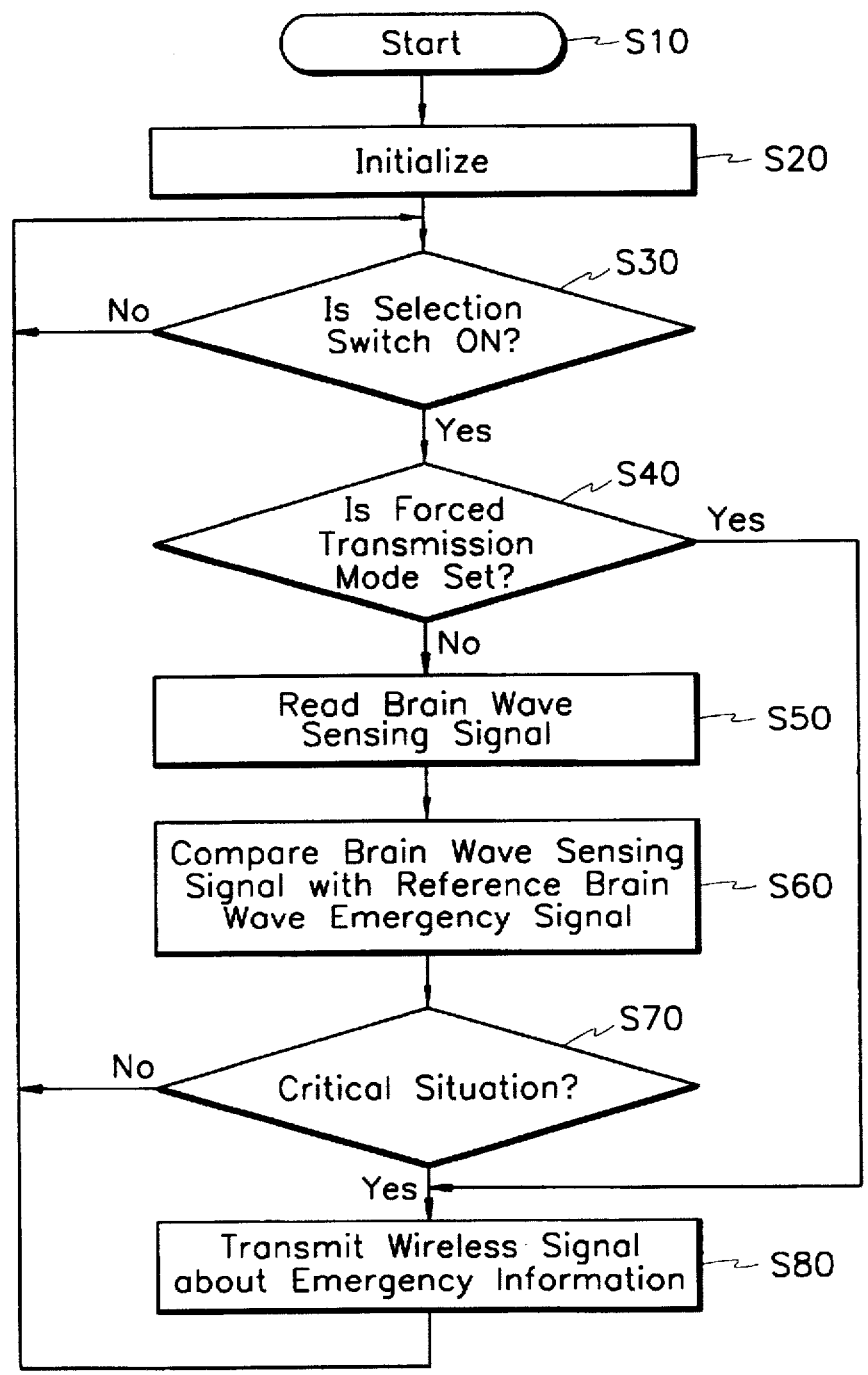
FIG. 2 is a flowchart illustrating the steps of the operational method for controlling an automatic transmission system using a driver's brain wave in accordance with the preferred embodiment of the present invention.

FIG. 2 is a flowchart illustrating the steps of the operational method for controlling an automatic transmission system using a driver's brain wave in accordance with the preferred embodiment of the present invention.

Referring to FIG. 2, a method for controlling the automatic transmission system of an emergency signal using a driver's brain wave includes the steps of starting an operation when electrical power is applied (Step S10); initializing all the variables (Step S20); determining whether the selection switch SW1 is turned ON (Step S30); determining whether a forced transmission mode is set when the selection switch SW1 is turned ON (Step S40); reading a brain wave sensing signal when the forced transmission mode is not set (Step S50); comparing the brain wave sensing signal with a reference brain wave emergency signal stored in the memory 50 (Step S60); determining whether a driver is in critical condition on the basis of a comparison result (Step S70); and transmitting a wireless signal about emergency information when the driver is in critical condition or the forced transmission mode is set (Step S80).

Next, the operation of the automatic transmission system of an emergency signal and a method using a driver's brain wave in accordance with the preferred embodiment of the present invention is explained hereinafter.

When power is applied, the method for controlling the automatic transmission system of an emergency signal using a driver's brain wave is performed by the micro-controller 40, whereby the operation of the automatic transmission system of an emergency signal using a driver's brain wave in accordance with the preferred embodiment of the present invention is started.

When the operation is started, the micro-controller 40 initializes all system variables in the memory 50 and determines whether the selection switch SW1 is turned ON.

The selection switch SW1 is for automatically transmitting an emergency signal as the driver's brain wave is automatically sensed by the micro-controller 40 by turning ON the selection switch SW1 when a driver wants to operate the automatic transmission system of an emergency signal using a driver's brain wave.

When the selection switch SW1 is turned ON, the micro-controller 40 determines whether the forced transmission mode is set, using a signal inputted from the forced transmission switch SW2.

The forced transmission switch SW2 is turned ON when an emergency signal is to be forcibly transmitted rather than according to sensing of the brain wave. Accordingly, when the life of the driver is not in danger but an emergency rescue operation is required after the accident, the authorities, the police, emergency units, and the hospital can be immediately notified of the emergency by tuning ON the forced transmission switch SW2, whereby the injured can be quickly transported to the hospital, thereby increasing their chance of survival.

When the forced transmission switch SW2 is not turned ON, the micro-controller 40 reads the brain wave sensing signal inputted by the analog/digital converter 30.

The brain wave sensing block 10 has a construction in that brain wave sensors 12 are attached to both end portions of a headphone-shaped mechanism 11. When the driver wears the headphone-shaped mechanism 11, the brain wave of the driver is sensed by the brain wave sensors 12, and the brain wave sensors 12 converts the brain wave into an electric signal and outputs the electric signal to the amplifier 20.

The amplifier 20 amplifies the brain wave sensing signal inputted from the brain wave sensing block 10 to a predetermined magnitude, and outputs the amplified signal to the analog/digital converter 30.

The analog/digital converter 30 converts an analog brain wave sensing signal inputted from the amplifier 20 into a digital brain wave sensing signal, and outputs the digital brain wave sensing signal to the micro-controller 40.

The micro-controller 40 compares the brain wave sensing signal inputted from the analog/digital converter 30 with the reference brain wave emergency signal stored in the memory 50, and determines whether the life of the driver is in danger.

A unique type of brain wave, generated when the life of a human being is in danger, is digitized and stored in the memory 50 as the reference brain wave emergency signal.

When the micro-controller 40 determines that the current situation is an emergency (for example, the driver is unconscious or the life of the driver is in danger after the accident), the micro-controller 40 transmits an information signal about the emergency to the transmission block 60 to transmit the information signal together with an information signal about the current location of the accident.

In addition, the micro-controller 40 transmits the information signal about the emergency to the transmission block 60 to transmit the information signal about the emergency together with the information signal about the current location of the accident, even when the life of the driver is not in danger but an emergency rescue is required, when the driver turns ON the forced transmission switch SW2.

When the information signal about the current location of the accident is inputted to the transmission block 60 together with the information signal about the emergency, the digital/analog converter 61 in the transmission block 60 converts the information signal about the current location of the accident and the information signal about the emergency, and outputs the converted signals to the modulator 63.

Besides the information signals inputted from the digital/analog converter 61, a carrier signal is inputted to the modulator 63 in the transmission block 63 from the carrier signal generator 62.

The modulator 63 outputs the modulated signal to the amplifier 64 by adding the analog information signal inputted from the digital/analog converter 61 on the carrier signal inputted from the carrier signal generator 62.

The amplifier 64 in the transmission block 60 amplifies the modulated signal inputted from the modulator 63 to a power level required for transmission, and outputs the amplified signal to the antenna 65, whereby the modulated signal may be put on the air from the antenna 65.

Figure 3:
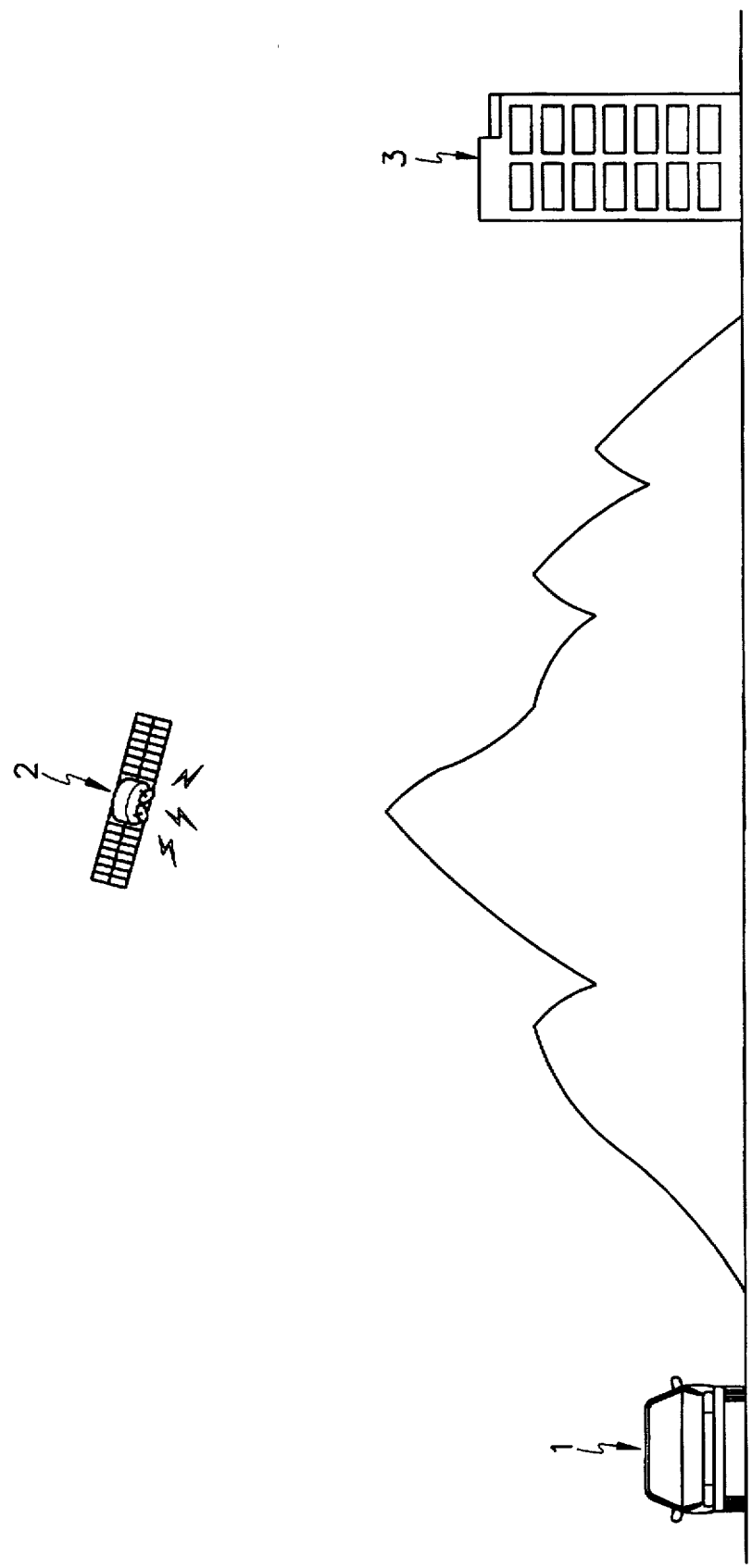
FIG. 3 is a view illustrating communication state between an earth station and a satellite and an automatic transmission system using a driver's brain wave in accordance with the preferred embodiment of the present invention.

The modulated signal outputted from the antenna 65 in the transmission block 60 is received by the GPS satellite 2 (as shown in FIG. 3), and transmitted again to an earth station 3 from the GPS satellite 2.

The earth station 3 perceives the information about the emergency of the driver or the information about the current location by demodulating the modulated signal after receiving the modulated signal from the GPS satellite 2.

FIG. 3 is a view illustrating a communication state between an earth station and a satellite and an automatic transmission system using a driver's brain wave in accordance with the preferred embodiment of the present invention.

Referring to FIG. 3, the earth station 3 transmits the information signals about the emergency of the driver or the current location of the accident to the police or the hospitals near the current location of the accident via the network.

As described above, the effect of the present invention lies in that the automatic transmission system of an emergency signal and a method thereof using a driver's brain wave which enables the police and the hospitals, having the network with the earth station, to provide the proper and immediate rescue operation for those involved in the accident by transmitting the emergency signal derived from the driver's brain wave to the earth station via the GPS satellite if the driver is in critical condition after the accident.

Other embodiments of the invention will be apparent to the skilled in the art from consideration of the specification and practice of the invention disclosed herein. It is intended that the specification and examples be considered as exemplary only, with the true scope and spirit of the invention being indicated by the following claims.

What is claimed is:

1. An automatic transmission system for sending an emergency signal based on a current condition of a human driver's brain wave, comprising:

means for sensing a brain wave generated by the human driver and for converting the brain wave into an electric brain wave signal;

an amplifier for amplifying the electric brain wave signal inputted from the brain wave sensing means;

an analog/digital converter for converting the analog brain wave signal inputted from the amplifier into a digital brain wave signal;

a memory for storing a digitized reference brain wave emergency signal representing a condition when the life of the driver is in danger;

a micro-controller for comparing the digital brain wave signal inputted from the analog/digital converter with the reference brain wave emergency signal stored in the memory, and for producing a first information signal representing the current location of the automatic transmission system and a second information signal representing emergency information when the life of the driver is in danger; and a transmission block for transmitting the first information signal and the second information signal by adding the information signals on a carrier signal of a high frequency.

2. The automatic transmission system of claim 1, further comprising a forced transmission switch for forcibly transmitting the information signals by turning ON the forced transmission switch when the life of the driver is not in danger but an emergency rescue operation is required.

3. A method for controlling an automatic transmission system for sending an emergency signal based on a current condition of a human driver's brain wave, comprising the steps of:

initializing all variables when electric power is applied;

determining whether a selection switch is turned ON;

reading a brain wave sensing signal of the driver's brain wave when the selection switch is turned ON;

determining whether the life of the driver is in danger after comparing the brain wave sensing signal with a reference brain wave emergency signal stored in a memory; and transmitting a wireless signal about an emergency when the life of the driver is in danger, the wireless signal including a current location of the automatic transmission system.

4. The method of claim 3, further comprising the steps of determining whether a forced transmission mode is set when the selection switch is turned ON, and forcibly transmitting a wireless signal about the emergency when the forced transmission mode is set, the wireless signal including the current location of the automatic transmission system.

* * * * *